US010256051B2

(12) United States Patent
Sanai et al.

(10) Patent No.: US 10,256,051 B2
(45) Date of Patent: Apr. 9, 2019

(54) BOARD UNIT, OPERATION INPUT UNIT, ENERGY TREATMENT INSTRUMENT, AND MANUFACTURING METHOD OF BOARD UNIT

(71) Applicant: OLYMPUS CORPORATION, Hachioji-shi, Tokyo (JP)

(72) Inventors: Hideo Sanai, Hachioji (JP); Yoshitaka Fujii, Atsugi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/584,524

(22) Filed: May 2, 2017

(65) Prior Publication Data
US 2017/0236659 A1 Aug. 17, 2017

Related U.S. Application Data

(63) Continuation of application No. PCT/JP2015/084547, filed on Dec. 9, 2015.

(30) Foreign Application Priority Data

Dec. 19, 2014 (JP) .................................. 2014-257663

(51) Int. Cl.
*H01H 9/04* (2006.01)
*H01H 9/02* (2006.01)
*H01H 11/00* (2006.01)
*H01H 13/06* (2006.01)
(Continued)

(52) U.S. Cl.
CPC ....... *H01H 9/04* (2013.01); *A61B 17/320068* (2013.01); *A61B 18/14* (2013.01);
(Continued)

(58) Field of Classification Search
CPC .... H01H 2221/01; H01H 25/008; H01H 3/02; H01H 13/14; H01H 19/14; H01H 3/38;
(Continued)

(56) References Cited

U.S. PATENT DOCUMENTS 7,439,460 B1 * 10/2008 Watson ................. B60R 16/005
200/18
2005/0016822 A1 * 1/2005 Mowatt ................. A01B 63/00
200/6 A
(Continued)

FOREIGN PATENT DOCUMENTS

JP     S55-100617 A    7/1980
JP     H05-31042 U     4/1993
(Continued)

OTHER PUBLICATIONS

Mar. 8, 2016 Search Report issued in International Patent Application No. PCT/JP2015/084547.
(Continued)

*Primary Examiner* — Ahmed M Saeed
(74) *Attorney, Agent, or Firm* — Oliff PLC (57) ABSTRACT

A switch board of a board unit includes a switch board including an exposed portion exposed to an outside, a non-exposed portion not exposed to the outside, and a switch provided in the non-exposed portion. The non-exposed portion of the switch board is covered with the cover portion. The cover portion is formed as one piece with the switch board in the state in which liquid-tightness is kept between the cover portion and the non-exposed portion, and liquid is prevented from flowing from the outside of the board unit into the non-exposed portion.

9 Claims, 9 Drawing Sheets (51) Int. Cl.
*A61B 18/14* (2006.01)
*A61B 17/32* (2006.01)
*H01H 13/70* (2006.01)
*H01H 13/86* (2006.01)
*H01H 13/88* (2006.01)
*A61B 17/00* (2006.01)
*A61B 18/00* (2006.01)

(52) U.S. Cl.
CPC .......... *A61B 18/1402* (2013.01); *H01H 9/02* (2013.01); *H01H 11/00* (2013.01); *H01H 13/06* (2013.01); *H01H 13/70* (2013.01); *H01H 13/86* (2013.01); *A61B 2017/00526* (2013.01); *A61B 2018/0091* (2013.01); *A61B 2018/0094* (2013.01); *A61B 2018/00601* (2013.01); *A61B 2018/00994* (2013.01); *H01H 13/88* (2013.01)

(58) Field of Classification Search
CPC ........ H01H 23/24; H01H 25/065; H01H 3/46; H01H 71/56
USPC ........... 200/6 A, 18, 331, 4, 5 R, 547, 51.28, 200/316, 5 E, 518, 531, 550
See application file for complete search history.

(56) References Cited

U.S. PATENT DOCUMENTS

| | | | |
|---|---|---|---|
| 2005/0045453 A1* | 3/2005 | Funada | G01D 5/34792 |
| | | | 200/5 R |
| 2005/0113824 A1 | 5/2005 | Sartor et al. | |
| 2018/0025878 A1* | 1/2018 | Dolecek | H01H 9/20 |
| | | | 200/331 |

FOREIGN PATENT DOCUMENTS

| | | |
|---|---|---|
| JP | H08-111132 A | 4/1996 |
| JP | 2005-56752 A | 3/2005 |
| JP | 2006-280956 A | 10/2006 |
| JP | 2006-302526 A | 11/2006 |
| JP | 2011-067631 A | 4/2011 |
| JP | 2013-192952 A | 9/2013 |

OTHER PUBLICATIONS

Jun. 20, 2017 International Preliminary Report on Patentability issued in International Patent Application No. PCT/JP2015/084547.

* cited by examiner

BOARD UNIT, OPERATION INPUT UNIT, ENERGY TREATMENT INSTRUMENT, AND MANUFACTURING METHOD OF BOARD UNIT

CROSS-REFERENCE TO RELATED APPLICATIONS

This is a Continuation Application of PCT Application No. PCT/JP2015/084547, filed Dec. 9, 2015 and based upon and claiming the benefit of priority from prior Japanese Patent Application No. 2014-257663, filed Dec. 19, 2014, the entire contents of which are incorporated herein by reference.

BACKGROUND OF THE INVENTION

1. Field of the Invention

The present invention relates to a board unit including a switch board which is provided with a switch. In addition, the invention relates to an operation input unit including the board unit, and an energy treatment instrument including the operation input unit. Furthermore, the invention relates to a manufacturing method of the board unit.

2. Description of the Related Art

U.S. Patent Application Publication No. 2005/0113824 discloses an energy treatment system including a switch board (board unit) which is provided with a switch. In an energy treatment instrument of this energy treatment system, a button portion is pushed by an operation input, and thereby an external force application portion (pusher) moves, and an external force acts on the switch from the external force application portion. Thereby, a movable contact portion and a fixed contact portion come in contact in the switch, and electrical conduction is established in the switch. By the electrical conduction in the switch being detected, high-frequency electric power is supplied to a treatment portion, and a high-frequency current flows through a treated target, such as a biological tissue, which is in contact with the treatment portion.

BRIEF SUMMARY OF THE INVENTION

According to one aspect of the invention, a board unit including: a switch board including an exposed portion which is exposed to an outside, a non-exposed portion which is not exposed to the outside, and a switch provided in the non-exposed portion; and a cover portion covering the non-exposed portion of the switch board, the cover portion being formed as one piece with the switch board in a state in which liquid-tightness is kept between the cover portion and the non-exposed portion, thereby preventing liquid from flowing from the outside into the non-exposed portion.

According to one another aspect of the invention, a manufacturing method of a board unit, including: inserting a sheet member, which forms a part of a cover portion, in a fixed side cavity of a fixed die; fixing a switch board on the fixed die in a state in which the sheet member is located in the fixed side cavity, and disposing the switch board on a receiving surface of the fixed die in a state in which the position of the switch board is set relative to the fixed die in an extension direction, a width direction and a thickness direction; closing a movable die relative to the fixed die in a state in which the switch board is disposed on the fixed die, and forming an injection cavity by the fixed side cavity of the fixed die and a movable side cavity of the movable die; and injecting a resin in the injection cavity, thereby forming the cover portion by the sheet member and the injected resin and forming a non-exposed portion, which is covered with the cover portion, at a position in the switch board, where at least a switch is disposed, the resin being injected in such a state that liquid-tightness is kept between the non-exposed portion and the cover position.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A first embodiment of the present invention will be described with reference to FIG. 1 and FIGS. 7A-D.

Figure 1:
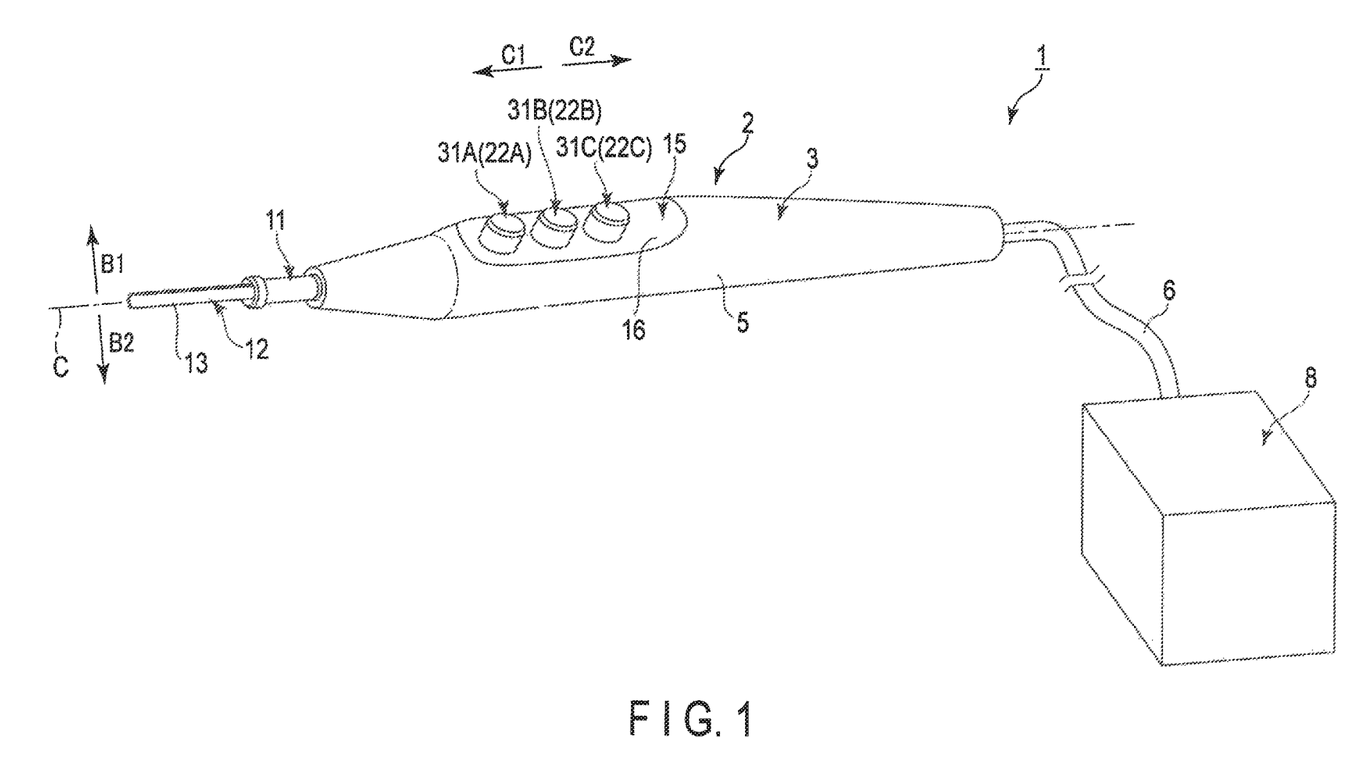
FIG. 1 is a perspective view which schematically illustrates an energy treatment system according to a first embodiment.

FIG. 1 is a view illustrating an energy treatment system (energy treatment apparatus) 1. As illustrated in FIG. 1, the energy treatment system 1 includes an energy treatment instrument (high-frequency treatment instrument) 2. The energy treatment instrument 2 has a longitudinal axis C. When a direction parallel to the longitudinal axis C is defined as a longitudinal axial direction, one side in the longitudinal axial direction is a distal side (arrow C1 side in FIG. 1), and a side opposite to the distal side is a proximal side (arrow C2 side in FIG. 1). The energy treatment instrument 2 includes a held unit 3 which extends along the longitudinal axis C. The hold unit 3 includes a held casing 5 which forms an exterior of the held unit 3. One end of a cable 6 is connected to the held unit 3. The other end of the cable 6 is detachably connected to an energy source unit 8. The energy source unit 8 is, for example, an energy control device. The energy source unit 8 includes an electric power source, a conversion circuit which converts electric power from the electric power source to high-frequency electric power (high-frequency electric energy), and a conversion circuit which converts electric power from the electric power source to vibration generating electric power (vibration generating electric energy). In addition, the energy source unit 8 is provided with a controller which is composed of a processor including a CPU (Central Processing Unit) or an ASIC (application specific integrated circuit), and a storage such as a memory.

In addition, a sheath 11 and a blade 12 are detachably coupled to the held unit 3 from the distal side. The sheath 11 and blade 12 extend along the longitudinal axis C, and are inserted into an inside of the held casing 5 from the distal side. The blade 12 is inserted through the sheath 11, and a distal portion of the blade 12 is provided with a treatment portion (end effector) 13 which projects from a distal end of the sheath 11 toward the distal side. In the inside of the held casing 5, a vibration generator (not shown) including an ultrasonic transducer is coupled to the proximal side of the blade 12. In the ultrasonic transducer, vibration generating electric power is supplied from the energy source unit 8, and thereby ultrasonic vibration is generated. The ultrasonic vibration generated by the ultrasonic transducer is transmitted to the distal side through the blade 12.

Figure 2:
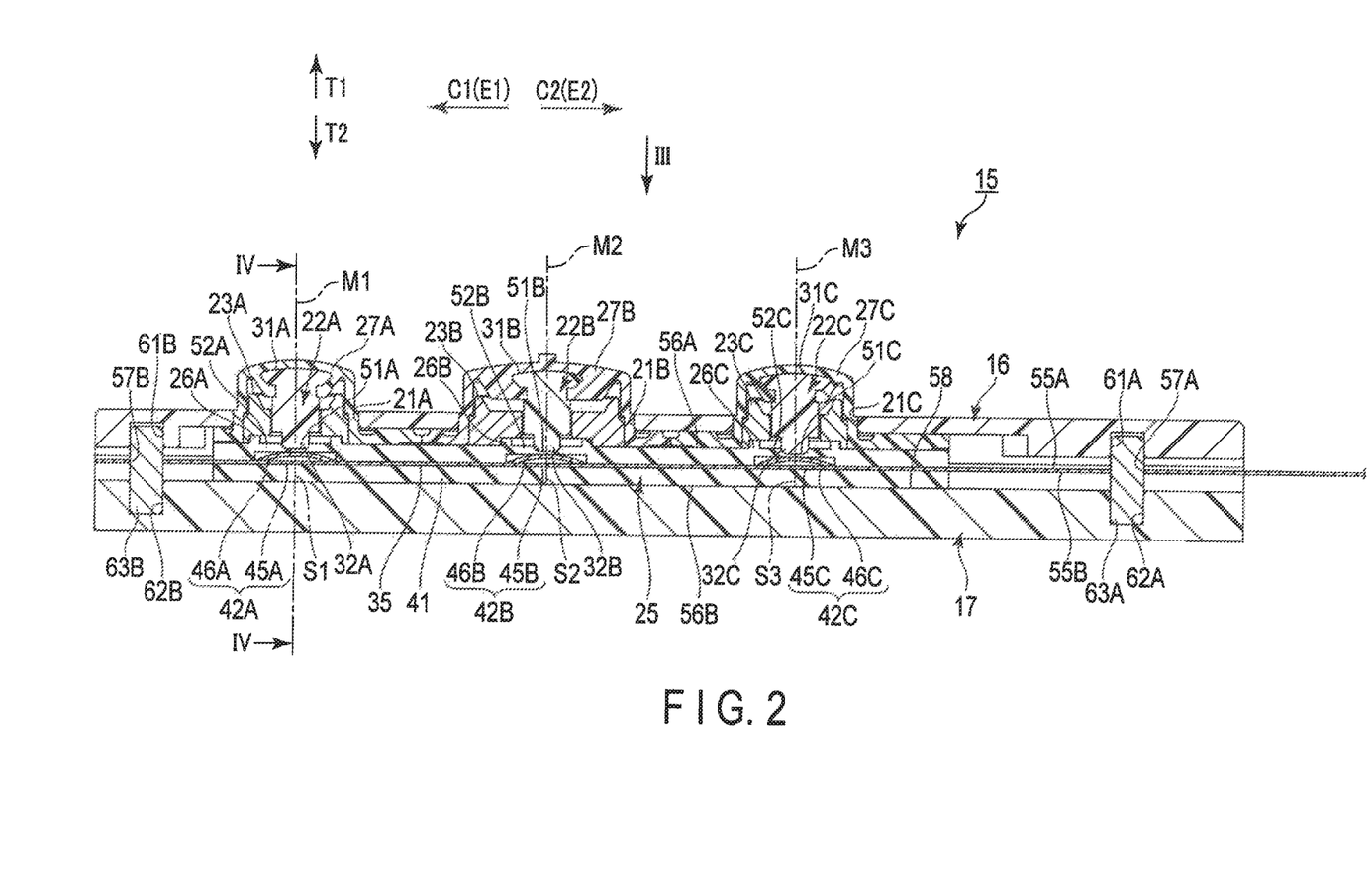
FIG. 2 is a cross-sectional view which schematically illustrates, in cross section perpendicular to a width direction of an energy treatment instrument, an operation input unit according to the first embodiment.
Figure 3:
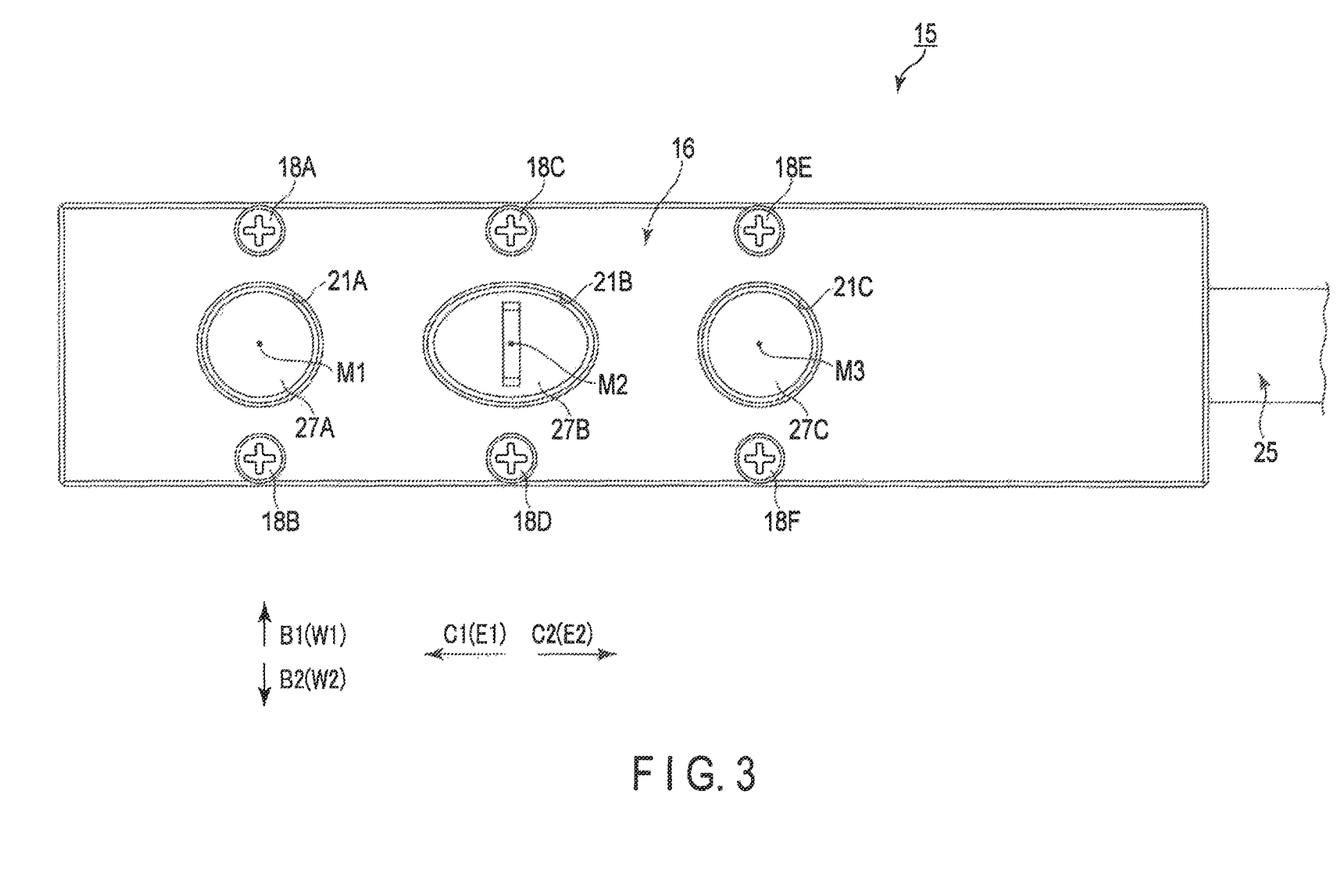
FIG. 3 is a schematic view, as viewed from a direction of an arrow III in FIG. 2.
Figure 4:
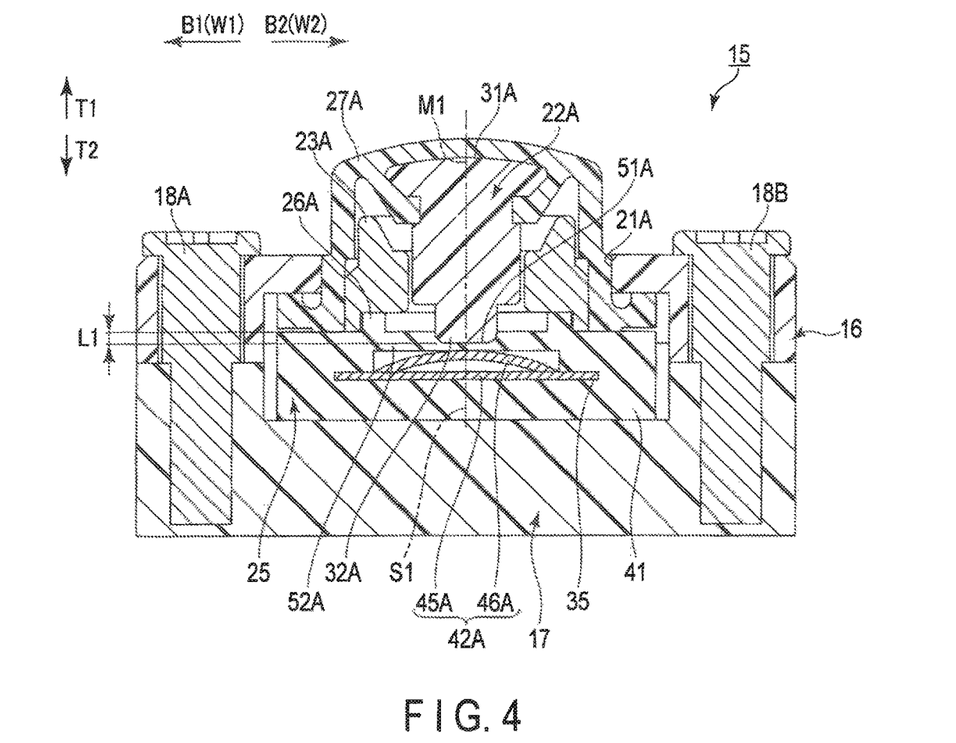
FIG. 4 is a cross-sectional view taken along line IV-IV in FIG. 2.

In the held unit 3, there is provided an operation input unit 15 to which an energy operation is input for supplying high-frequency electric power (and ultrasonic vibration) to the treatment portion 13 (blade 12) as energy for use in a treatment. Using the supplied high-frequency electric power, the treatment portion 13 treats a treated target such as a biological tissue. FIG. 2 to FIG. 4 are views illustrating a configuration of the operation input unit 15. Here, a certain direction crossing (perpendicular to) the longitudinal axial direction (directions of an arrow B1 and an arrow B2 in FIG. 1) is defined as a width direction of the energy treatment instrument 2. FIG. 2 illustrates a cross section perpendicular to the width direction of the energy treatment instrument 2. In addition, FIG. 3 is a view, as viewed from a direction of an arrow III in FIG. 2, and FIG. 4 is a cross-sectional view taken along line IV-IV in FIG. 2.

As illustrated in FIG. 2 to FIG. 4, the operation input unit 15 includes a unit exterior portion 16 which forms a part of the held casing 5. In addition, the operation input unit 15 includes a base 17 which is disposed in the inside of the held casing 5. The base 17 is fixed to the unit exterior portion 16 via fixing pins 18A to 18F (six fixing pins in this embodiment).

In addition, through-holes 21A to 21C (three through-holes in this embodiment), which penetrate from the inside of the held casing 5 to the outside, are formed in the unit exterior portion 16. A pusher (corresponding one of 22A to 22C) and a support member (corresponding one of 23A to 23C) are disposed in each of the through-holes 21A to 21C.

Each of the pushers (shaft members) 22A to 22C is inserted in the support member (corresponding one of 23A to 23C), and each of the support members 23A to 23C is formed in such a cylindrical shape as to surround the pusher (corresponding one of 22A to 22C). Each of the pushers 22A to 22C has a movement axis (corresponding one of M1 to M3), and is movable along the movement axis (corresponding one of M1 to M3) relative to the unit exterior portion 16, base 17 and support member (corresponding one of 23A to 23C). In the present embodiment, the movement axes M1 to M3 cross (are perpendicular to) the longitudinal axial direction, and cross (are perpendicular to) the width direction of the energy treatment instrument 2.

Figure 5:
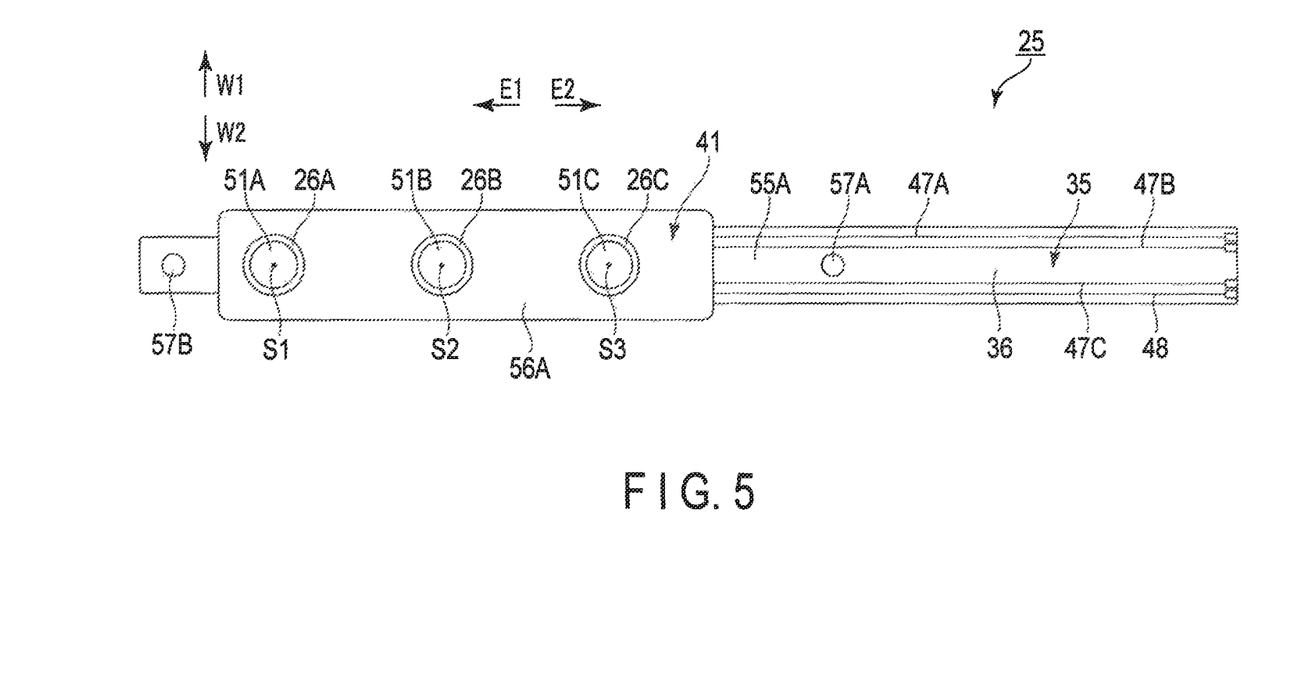
FIG. 5 is a schematic view illustrating a board unit according to the first embodiment, as viewed from one side of a thickness direction.
Figure 6:
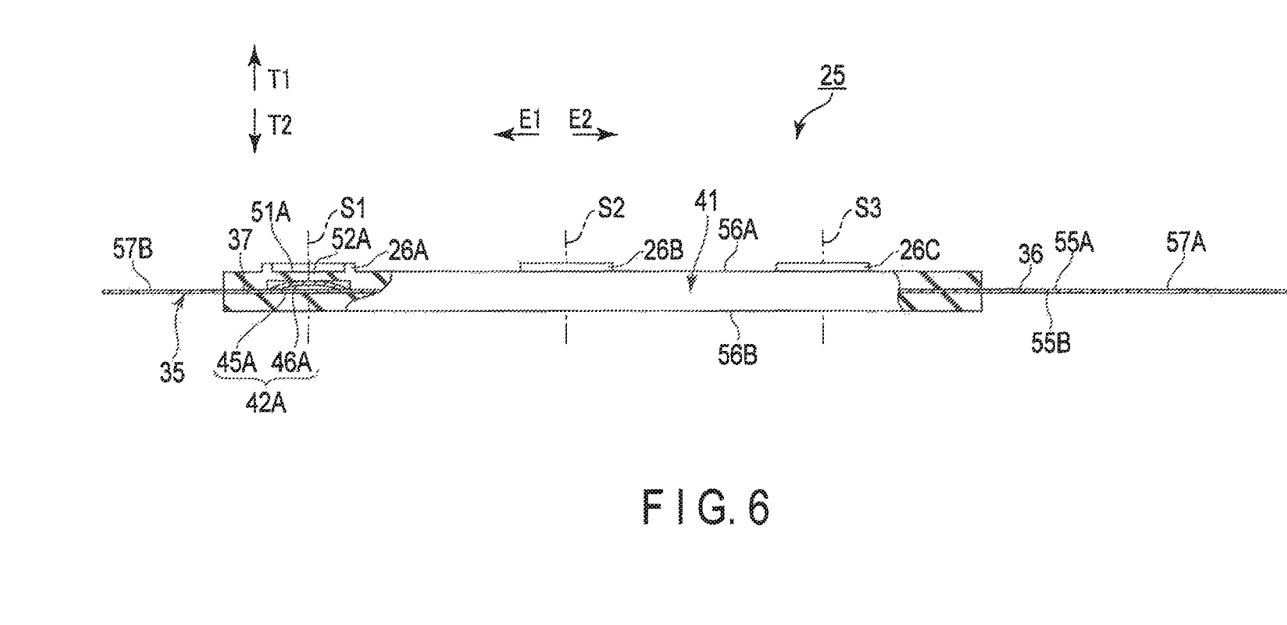
FIG. 6 is a schematic view illustrating the board unit according to the first embodiment, as viewed from one side of a width direction, FIG. 6 showing a partial cross section perpendicular to the width direction.
Figure 7A:
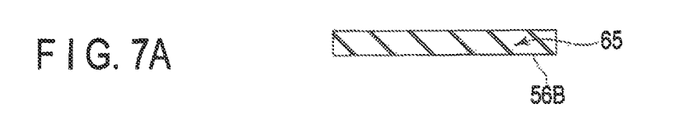
FIGS. 7A-7D are a series of schematic views illustrating a manufacturing method of the board unit according to the first embodiment.
Figure 7B:
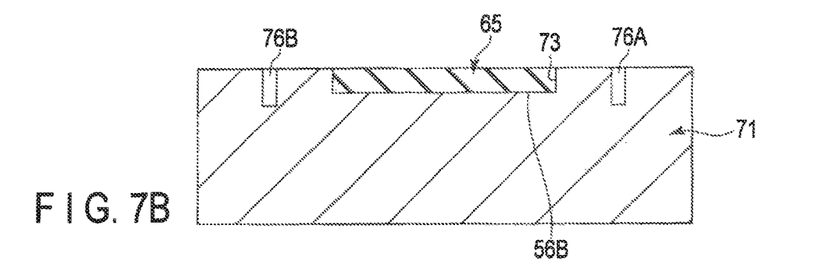
Figure 7C:
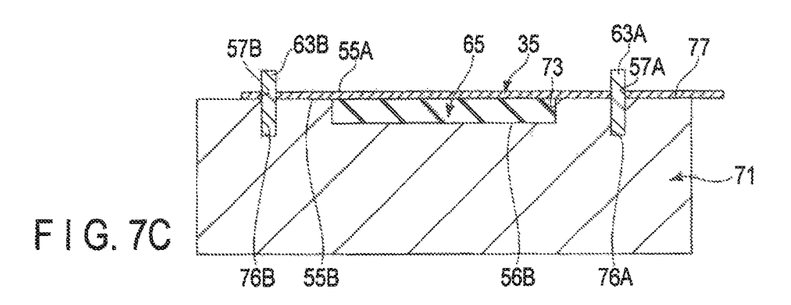
Figure 7D:
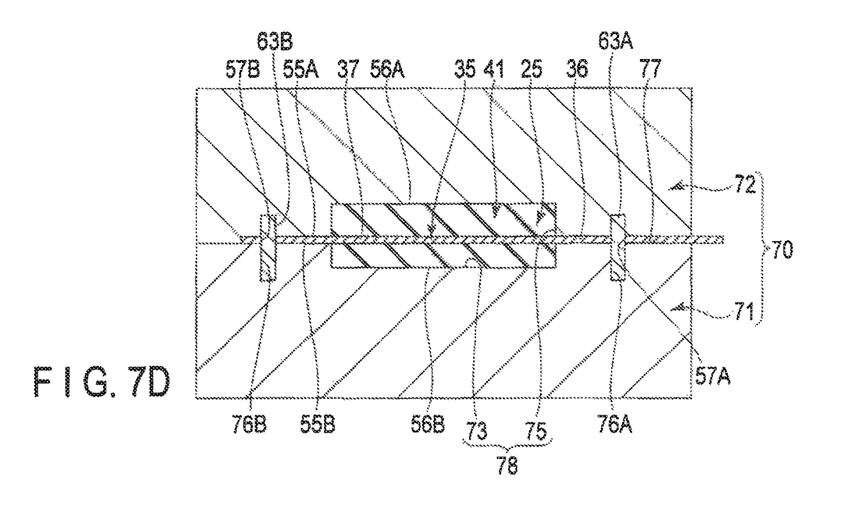

The operation input unit 15 includes a board unit 25 which is disposed between the unit exterior portion 16 and base 17. FIG. 5 and FIG. 6 are views illustrating the configuration of the board unit 25. As illustrated in FIGS. 2, 3, 5 and 6, the board unit 25 extends along an extension direction (a direction of an arrow E1 and a direction of an arrow E2 in each of FIG. 5 and FIG. 6). In this embodiment, the extension direction of the board unit 25 substantially agrees with the longitudinal axial direction (the distal side and proximal side) of the energy treatment instrument 2. In addition, in the board unit 25, a certain direction perpendicular to (crossing) the extension direction is defined as a width direction of the board unit 25 (directions of an arrow W1 and an arrow W2 in FIG. 5). Besides, in the board unit 25, a direction perpendicular to (crossing) the extension direction and perpendicular to (crossing) the width direction is defined as a thickness direction of the board unit 25 (directions of an arrow T1 and an arrow T2 in FIG. 6). In the present embodiment, the width direction of the board unit 25 substantially agrees with the width direction of the energy treatment instrument 2. Incidentally, FIG. 5 is a view illustrating the board unit 25, as viewed from one side of the thickness direction (the unit exterior portion 16 side). In addition, FIG. 6 is a view illustrating the board unit 25, as viewed from one side of the width direction, FIG. 6 showing a partial cross section perpendicular to the width direction of the board unit 25.

The board unit 25 is disposed on the base 17. The board unit 25 is provided with engaging projection portions 26A to 26C (three engaging projection portions in this embodiment) which project toward the unit exterior portion 16. Each of the engaging projection portions 26A to 26C is formed in such a cylindrical shape as to surround the movement axis (corresponding one of M1 to M3) of the pusher (corresponding one of 22A to 22C). Each of the support members 23A to 23C is fixed to the board unit 25 by being engaged with the engaging projection portion (corresponding one of 26A to 26C).

The operation input unit 15 includes cover members 27A to 27C. In each of the through-holes 21A to 21C, the pusher (corresponding one of 22A to 22C) and the support member (corresponding one of 23A to 23C) are covered with the cover member (corresponding one of 27A to 27C). Thus, the pushers 22A to 22C and support members 23A to 23C are not exposed to the outside of the held casing 5. In addition, that part of each of the cover members 27A to 27C, which is located in a part other than the through-hole (corresponding one of 21A to 21C), is clamped between the unit exterior portion 16 and board unit 25.

Each of the pushers (shaft members) 22A to 22C includes a button portion (corresponding one of 31A to 31C) which is pushed by a surgeon or the like via the cover member, 27A to 27C, in the input (operation input) of an energy operation. By the button portion (corresponding one of 31A to 31C)

being pushed, each of the pushers 22A to 22C moves along the movement axis (corresponding one of M1 to M3). The movement axes M1 to M3 are substantially parallel to the thickness direction of the board unit 25. In addition, each of the pushers 22A to 22C includes an external force application portion (corresponding one of 32A to 32C) which is provided to be capable of pushing the board unit 25 in accordance with a pushing operation of the button portion (corresponding one of 31A to 31). In each of the pushers 22A to 22C, the external force application portion (corresponding one of 32A to 32C) pushes the board unit 25, thereby exerting an external force on the board unit 25. Besides, in each of the pushers 22A to 22C, the external force application portion (corresponding one of 32A to 32C) moves along the movement axis (corresponding one of M1 to M3) by the button portion (corresponding one of 31A to 31C) being pushed. Furthermore, in each of the pushers 22A to 22C, the pushing state of the board unit 25 by the external force application portion (corresponding one of 32A to 32C) varies by the movement of the external force application portion (corresponding one of 32A to 32C). The external force, which is exerted on the board unit 25 from each of the pushers 22A to 22C, varies in accordance with the pushing state of the board unit 25 by the eternal force application portion (corresponding one of 32A to 32C).

As illustrated in FIG. 2 to FIG. 6, the board unit 25 includes a switch board 35. The switch board 35 is, for example, a flexible printed board (FPC: flexible printed circuits), but may be a rigid board. The switch board 35 includes an exposed portion. 36 which is exposed to the outside of the board unit 25, and a non-exposed portion 37 which is not exposed to the outside of the board unit 25. In addition, the board unit 25 includes a cover portion 41 which covers the non-exposed portion 37 of the switch board 35. The cover portion 41 covers the non-exposed portion 37 from both sides in the thickness direction of the board unit 25. The cover portion 41 is formed of, for example, silicone rubber. In the present embodiment, the entirety of the cover portion 41 is formed of an elastic material. In addition, in this embodiment, the engaging projection portions 26A to 26C are formed in that part of the cover portion 41, which faces the unit exterior portion 16 side.

Switches 42A to 42C (three switches in this embodiment) are provided in the non-exposed portion 37 of the switch board 35. Each of the switches 42A to 42C has a center axis (corresponding one of S1 to S3) along the thickness direction of the board unit 25. The center axis (corresponding one of S1 to S3) of each of the switches 42A to 42C is substantially coaxial with the movement axis (corresponding one of M1 to M3) of the pusher (corresponding one of 22A to 22c). Thus, each of the engaging projection portions 26A to 26C is formed in such a cylindrical shape as to surround the center axis (corresponding one of S1 to S) of the switch (corresponding one of 42A to 42C)

Each of the switches 42A to 42C includes a fixed contact portion (corresponding one of 45A to 45C) which is fixed to the switch board 35, and a movable contact portion (corresponding one of 46A to 46C) which is provided to be capable of moving (movable) relative to the fixed contact portion (corresponding one of 45A to 45C). Each of the fixed contact portions (fixed contact point portions) 45A to 45C is located on a side near the base 17 in the thickness direction of the board unit 25, with respect to the movable contact portion (corresponding one of 46A to 46C). The movable contact portions (movable contact point portions) 46A to 46C are formed of a material having elasticity and electrical conductivity, and the cover portion 41 abuts on the movable contact portions 46A to 46C from the unit exterior portion 16 side in the thickness direction of the board unit 25.

Besides, on the switch board 35, electrical path portions 47A to 47C, 48 are formed along the extension direction of the board unit 25 (in this embodiment, from the proximal side to distal side of the energy treatment instrument 2). Each of the electrical path portions 47A to 47C, 48 is electrically connected to the controller (not shown) of the energy source unit 8 via a corresponding electrical wiring (not shown) which extends through the inside of the cable 6. The electrical path portion 47A is electrically connected to the movable contact portion 46A, and the electrical path portion 47B is electrically connected to the movable contact portion 46B. In addition, the electrical path portion 47C is electrically connected to the movable contact portion 46C. Furthermore, the electrical path portion 48 is electrically connected to all of the fixed contact portions 45A to 45C, and is commonly used as a ground line of all of the switches 42A to 42C.

Each of the external force application portions 32A to 32C (pushers 22A to 22C) abuts on an outer surface which faces the unit exterior portion 16 side in the cover portion 41. Specifically, the outer surface of the cover portion 41 is provided with abutment surface portions (pusher abutment portions) 51A to 51C, and the external force application portion (corresponding one of 32A to 32C) of the pusher (corresponding one of 22A to 22C) abuts on each of the abutment surface portions 51A to 51C. Here, in each of the pushers 22A to 22C, a state in which the button portion (corresponding one of 31A to 31C) is not pushed (i.e. a state in which no energy operation is input) is defined as a neutral state (non-pushed state). In each of the pushers 22A to 22C in this embodiment, even in the neutral state (neutral position), the external force application portion (corresponding one of 32A to 32C) abuts on the corresponding abutment surface portion (corresponding one of 51A to 51C). In addition, in each of the pushers 22A to 22C, in the neutral state, a balanced state occurs in which the pushing force (external force) from the external force application portion (corresponding one of 32A to 32C) to the cover portion 41 and the reactive force (elastic force) from the cover portion 41 are balanced. Thus, in the neutral state, each of the pushers 22A to 22C does not move along the movement axis (corresponding one of M1 to M3).

In each of the pushers 22A to 22C, the button portion (corresponding one of 31A to 31C) is pushed (i.e. the energy operation is input), and the external force application portion (corresponding one of 32A to 32C) moves from the neutral state, and thereby the external force acting on the cover portion. 41 varies. The cover portion 41 is provided with elastic deformation portions 52A to 52C (three elastic deformation portions in this embodiment), and each of the elastic deformation portions 52A to 52C elastically deforms in accordance with a variation of the external force (pushing force) from the pusher (corresponding one of 22A to 22C). Here, the shape of each of the elastic deformation portions 52A to 52C at a time of the neutral state of the corresponding pusher (corresponding one of 22A to 22C) is defined as a neutral shape. Each of the elastic deformation portions 52A to 52C elastically deforms from the neutral shape (toward the arrow T2 side) by the external force (pushing force) from the pusher (corresponding one of 22A to 22C) being increased (varied) by the input of the energy operation. In the present embodiment, the abutment surface portion (corresponding one of 51A to 51C), on which the pusher (corresponding one of 22A to 22C) abuts, is provided on the outer surface of each of the elastic deformation portions 52A to 52C.

In addition, in the present embodiment, each of the elastic deformation portions 52A to 52C abuts on the movable contact portion (corresponding one of 46A to 46C) of the corresponding switch (corresponding one of 42A to 42C) from the unit exterior portion 16 side. In each of the switches 42A to 42C, when the elastic deformation portion (corresponding one of 52A to 52C) is in the neutral shape (i.e. when the pusher (corresponding one of 22A to 22C) is in the neutral state), the movable contact portion (corresponding one of 46A to 46C) is not in contact with the fixed contact portion (corresponding one of 45A to 45C). Each of the elastic deformation portions 52A to 52C elastically deforms from the neutral shape (toward the arrow T2 side), thereby exerting a pushing force on the corresponding switch (corresponding one of 42A to 42C). In addition, in each of the switches 42A to 42C, by the pushing force acting from the elastic deformation portion (corresponding one of 52A to 52C) onto the movable contact portion (corresponding one of 46A to 46C), the movable contact portion (corresponding one of 46A to 46C) elastically deforms (toward the arrow T2 side), and the movable contact portion (corresponding one of 46A to 46C) comes in contact with the fixed contact portion (corresponding one of 45A to 45C).

The controller (not shown) of the energy source unit 8 detects the open or closed state of each of the switches 42A to 42C, thereby detecting the presence or absence of the input of the energy operation in the corresponding button portion (corresponding one of 31A to 31C). If the energy operation is input in the button portion 31A and the switch 42A enters the closed state (i.e. if the fixed contact portion 45A and movable contact portion 46A come in contact), the electrical path portion 47A and electrical path portion 48 are electrically connected and electrical conduction is established in the switch 42A. At this time, the energy source unit 8 detects the flow of electric current (detection current) through the electrical path portion 47A and electrical path portion 48, thereby detecting the input of the energy operation in the button portion 31A. In addition, if the energy operation is input in the button portion 31B and the switch 42B enters the closed state, the electrical path portion 47B and electrical path portion 48 are electrically connected in the switch 42B. At this time, the energy source unit 8 detects the flow of electric current (detection current) through the electrical path portion 47B and electrical path portion 48, thereby detecting the input of the energy operation in the button portion 31B. Furthermore, if the energy operation is input in the button portion 31C and the switch 42C enters the closed state, the electrical path portion 47C and electrical path portion 8 are electrically connected in the switch 42C. At this time, the energy source unit 8 detects the flow of electric current (detection current) through the electrical path portion 47C and electrical path portion 48, thereby detecting the input of the energy operation in the button portion 31C. Accordingly, when the switch (corresponding one of 42A to 42C) is in the closed state, an electric current, which is supplied to the switch (corresponding one of 42A to 42C), passes through each of the electrical path portions 47A to 47C. Current passes through the electrical path portion 48, when any one of the switches 42A to 42C is in the closed state.

If the input of the energy operation in the button portion 31A of the pusher 22A is detected, a high-frequency electric power is output from the energy source unit 8, and the high-frequency electric power is supplied to the treatment portion 13 (blade 12). In this state, the treatment portion 13 is brought into contact with a treated target such as a biological tissue, and thereby a high-frequency current flows between the treatment portion 13 and a counter-electrode plate (not shown) through the treated target. When the energy operation was input in the button portion 31A, a high-frequency current of a continuous waveform flows to the treated target, and the treated target is cut and opened. Also when the input of the energy operation in the button portion 31C of the pusher 22C was detected, a high-frequency electric power is supplied to the treatment portion 13. However, when the energy operation was input in the button portion 31C, a high-frequency current of not a continuous waveform but a burst waveform flows to the treated target, and the treated target is coagulated. In addition, when the input of the energy operation in the button portion 31B of the pusher 22B was detected, a high-frequency electric power is supplied to the treatment portion 13, and also a vibration generating electric power is supplied to an ultrasonic transducer (not shown) and ultrasonic vibration is transmitted to the treatment portion 13. In the treatment portion 13, the treated target is cut and opened by using the ultrasonic vibration, and the high-frequency current of the burst waveform is passed through the treated target and the treated target is coagulated.

If the button portion (corresponding one of 31A to 31C) is no longer pushed by the surgeon (i.e. if the input of the energy operation is released), each of the pushers 22A to 22C returns to the position of the neutral state (balanced state). By the corresponding pusher (corresponding one of 22A to 22C) moving to the neutral state (non-pushed state), each of the elastic deformation portions 52A to 52C restores (elastically restores) to the neutral shape. By the corresponding elastic deformation portion (corresponding one of 52A to 52C) restoring to the neutral shape, the pushing force stops acting on each of the switches 42A to 42C from the elastic deformation portion (corresponding one of 52A to 52C), and the movable contact portion (corresponding one of 46A to 46C) is separated from (comes out of contact with) the fixed contact portion (corresponding one of 45A to 45C).

Specifically, by the corresponding elastic deformation portion (corresponding one of 52A to 52C) restoring to the neutral shape, each of the switches 42A to 42C enters the open state. When all of the switches 42A to 42C are in the open state, the supply of high-frequency electric power to the treatment portion 13 from the energy source unit 8 is stopped, and the supply of vibration generating electric power to the ultrasonic transducer is also stopped.

In the board unit 25, the cover portion 41 is formed as one piece with the switch board 35. In addition, in the board unit 25, liquid-tightness is kept between the non-exposed portion 37 of switch board 35 and the cover portion 41. Thus, liquid is prevented from flowing from the outside of the board unit 25 into the non-exposed portion 37 which is located inside the cover portion 41.

The switch board 35 of the board unit 25 includes a board surface (first board surface) 55A which faces the unit exterior portion 16 side in the thickness direction of the board unit 25, and a board surface (second board surface) 55B which faces the base 17 side in the thickness direction of the board unit 25. The switches 42A to 42C and electrical path portions 47A to 47C, 48 are disposed on the board surface 55A. In addition, the board surface 55B is formed substantially planar. Besides, the cover portion 41 includes a cover portion outer surface (first cover portion outer surface) 56A which faces the unit exterior portion 16 side in the thickness direction of the board unit 25, and a cover portion outer surface (second cover portion outer surface) 56B which faces the base 17 side in the thickness direction of the board unit 25. In the present embodiment, the abutment surface portion, 51A to 51C, on which the corresponding pusher (corresponding one of 22A to 22C) abuts, is provided on the cover portion outer surface 56A. In addition, the cover portion outer surface 56B is formed substantially planar.

Besides, a first hole 57A and a second hole 57B, which penetrate the switch board 35 in the thickness direction of the board unit 25, are formed in the board unit 25. The first hole 57A and second hole 57B penetrate the switch board 35 from the board surface 55A to the board surface 55B in the exposed portion 36 of the switch board 35. Accordingly, the first hole 57A and second hole 57B penetrate the board unit 25 in the thickness direction of the board unit 25. In addition, in the present embodiment, the first hole 57A is located on the proximal side with respect to the proximal end of the cover portion 41, and the second hole 57B is located on the distal side with respect to the distal end of the cover portion 41. Accordingly, the second hole 57B is located at a position spaced apart from the first hole 57A in the extension direction of the board unit 25.

On the inner surface of the unit exterior portion. 16, a recess portion (first inner surface recess portion) 61A is provided at a position opposed to the first hole 57A, and a recess portion (second inner surface recess portion) 61B is provided at a position opposed to the second hole 57B. In addition, the base 17 includes an installation surface 58 on which the board unit 25 is disposed. In the installation surface 58 of the base 17, a recess portion (first base recess portion) 62A is provided at a position opposed to the first hole 57A, and a recess portion (second base recess portion) 62B is provided at a position opposed to the second hole 57B. A fixing pin (first fixing pin) 63A, which extends in the thickness direction of the board unit 25, is inserted through the first hole 57A. In addition, one end of the fixing pin 63A is engaged in the recess portion 61A of the unit exterior portion 16, and the other end thereof is engaged in the recess portion 62A of the base 17. Besides, a fixing pin (second fixing pin) 63B, which extends in the thickness direction of the board unit 25, is inserted through the second hole 57B. In addition, one end of the fixing pin 63B is engaged in the recess portion 61B of the unit exterior portion 16, and the other end thereof is engaged in the recess portion 62B of the base 17. Accordingly, the board unit 25 is attached to the unit exterior portion 16 and base 17 via the fixing pins 63A and 63B.

In the extension direction and width direction, the position of the board unit 25 is set at a position where the first hole 57A is opposed to the recess portion 61A of the unit exterior portion 16 and to the recess portion 62A of the base 17, and where the second hole 57B is opposed to the recess portion 61B of the unit exterior portion 16 and to the recess portion 62B of the base 17. Specifically, the first hole 57A or second hole 57B functions as a first position setting portion which sets the position in the extension direction of the board unit 25 relative to the base 17. In addition, the first hole 57A and second hole 57B cooperate and function as a second position setting portion which sets the position in the width direction of the board unit 25 relative to the base 17. The position of the board unit 25 is set relative to the unit exterior portion 16 and base 17 in the extension direction and width direction by the first hole 57A and second hole 57B, and thereby the center axis (corresponding one of S1 to S3) of each of the switches 42A to 42C becomes substantially coaxial with the movement axis (corresponding one of M1 to M3) of the corresponding pusher (corresponding one of 22A to 22C).

In addition, the cover portion outer surface 56B of the cover portion 41, which is substantially planar, abuts on the installation surface 58 of the base 17. By the cover portion outer surface 56B abutting on the installation surface 58 of the base 17, the position of the board unit 25 is set in the thickness direction relative to the unit exterior portion 16 and base 17. Specifically, the cover portion outer surface (second cover portion outer surface) 56B of the cover portion 41 functions as a third position setting portion which sets the position in the thickness direction of the board unit 25 relative to the base 17.

Besides, as described above, in the neutral state in which the button portion 31A is not pushed (i.e. in the neutral shape of the elastic deformation portion 52A), the external force application portion 32A abuts on the abutment surface portion 51A. Thus, even in the neutral state of the pusher 22A, the pushing force (external force) from the external force application portion 32A acts on the abutment surface portion 51A of the cover portion 41. Accordingly, as illustrated in FIG. 4, even in the neutral state of the pusher 22A, the abutment surface portion 51A is recessed on the cover portion outer surface (first cover portion outer surface) 56A of the cover portion 41 by a recess dimension L1 toward the base 17 side. Specifically, the pusher 22A laps with the abutment surface portion 51A by the recess dimension (lapping amount) L1. Here, the recess dimension L1 is, for example, 0.2 mm to 0.3 mm. Similarly, in the neutral state of the pusher 22B, the abutment surface portion 51B is recessed by a recess dimension L2 (not shown) toward the base 17 side by the pushing force (external force) from the external force application portion 32B. Also in the neutral state of the pusher 22C, the abutment surface portion 51C is recessed by a recess dimension L3 (not shown) toward the base 17 side by the pushing force (external force) from the external force application portion 32C. In the meantime, in each of the abutment surface portions 51A to 51C, by adjusting the recess dimension (corresponding one of L1 to L3), the pushing force on the corresponding button portion (corresponding one of 31A to 31C) at the time of setting the corresponding switch (corresponding one of 42A to 42C) in the closed state is adjusted. For example, by increasing the recess dimension (lap amount) L1 of the abutment surface portion 51A, it becomes possible to set the switch 42A in the closed state (ON state) even if the pushing force on the button portion 31A is small.

Next, a manufacturing method of the board unit 25 will be described. FIGS. 7A-D illustrate a manufacturing method of the board unit 25. As illustrated in FIGS. 7A-D, to start with, when the board unit 25 is manufacturing, a sheet member 65, which will serve as a part of the cover portion 41, is formed of, for example, silicone rubber. The sheet member 65 forms that part of the cover portion 41, which is located on the base 17 side with respect to the switch board 35. Accordingly, the cover portion outer surface (second cover portion outer surface) 56B of the cover portion 41 is formed by the sheet member 65.

The board unit 25 is formed by using a metal mold 70 including a fixed die 71 and a movable die 72. A fixed side cavity 73 is formed in the fixed die 71, and a movable side cavity 75 is formed in the movable die 72. The formed sheet member 65 is inserted (dropped) in the fixed side cavity 73 of the fixed die 71. Then, in the state in which the sheet member 65 is inserted in the fixed side cavity 73, the switch board 35 is fixed on the fixed die 71.

Engaging holes 76A and 76B are formed in the fixed die 71. The position of the switch board 35 is set relative to the fixed die 71 in the extension direction and width direction in the state which the first hole 57A is opposed to the engaging hole 76A, and the second hole 57B is opposed to the engaging hole 76B. Specifically, the first hole 57A and second hole 57B function as a position setting portion which sets the position of the switch board 35 relative to the fixed die 71 (fixed side cavity 73) and sheet member 65. In addition, the switch board 35 is fixed to the fixed die 71 by engaging the fixing pin 63A, which is inserted through the first hole 57A, with the engaging hole 76A, and by engaging the fixing pin 63B, which is inserted through the second hole 57B, with the engaging hole 76B.

At this time, the substantially planar board surface (second board surface) 55B of the switch board 35 abuts on a receiving surface 77 of the fixed die 71. By the board surface 55B abutting on the receiving surface 77 of the fixed die 71, the position of the switch board 35 is set in the thickness direction relative to the fixed die 71. Specifically, the board surface 55B functions as a position setting portion which sets the position in the thickness direction of the switch board 35 relative to the fixed die 71.

The movable die 72 is closed relative to the fixed die 71 in the state in which the position of the switch board 35 is set relative to the fixed die 71 in the extension direction, width direction and thickness direction.

Thereby, an injection cavity 78 is formed by the fixed side cavity 73 and movable side cavity 75 in the fixed die 71 and movable die 72. In addition, silicone rubber (resin) is injected in the injection cavity 78, and the cover portion 41 is formed. Thereby, the board unit 25 is formed. In this case, in a state in which liquid-tightness is kept between the non-exposed portion 37 of the switch board 35, which is covered with the cover portion 41, and the cover portion 41, the silicone rubber is injected and the switch board 35 and cover portion 41 are formed as one piece. In addition, since the injection is performed in the state in which the position of the switch board 35 is set relative to the fixed die 71 in the extension direction, width direction and thickness direction, the switch board 35 is covered with the cover portion 41 in proper positions in the extension direction, width direction and thickness direction. Accordingly, those positions of the switch board 35, in which the switches 42A to 42C are disposed, are properly covered with the cover portion 41.

In addition, when the board unit 25 is disposed on the base 17, the fixing pin 63A, which is inserted through the first hole 57A, is engaged with the recess portion 62A of the base 17, and the fixing pin 63B, which is inserted through the second hole 57B, is engaged with the recess portion 62B of the base 17. Thereby, the board unit 25 is fixed to the base 17. In addition, by engaging the fixing pin 63A with the recess portion 61A of the unit exterior portion 16, and by engaging the fixing pin 63B with the recess portion 61B of the unit exterior portion 16, the board unit 25 is fixed to the unit exterior portion 16. Here, in the board unit 25, the cover portion 41 prevents the flow of liquid from the outside into the non-exposed portion 37 (switches 42A to 42C) of the switch board 35. Thus, when the board unit 25 is assembled to the base 17 and unit exterior portion 16, there is no need to perform, for example, a work of potting a filler between each of the switches 42A to 42C and the pusher (corresponding one of 22A to 22C). Therefore, the disposition and assembly of the board unit 25 to the base 17 and unit exterior portion. 16 can easily be performed, and the operation input unit 15 including the board unit 25 can easily be assembled.

Additionally, the position of the board unit 25 is set in the extension direction and width direction at such a position that the first hole 57A is opposed to the recess portion 61A of the unit exterior portion 16 and the recess portion 62A of the base 17, and that the second hole 57B is opposed to the recess portion 61B of the unit exterior portion 16 and the recess portion 62B of the base 17. Since the board unit 25 is positioned relative to the unit exterior portion 16 and base 17 in the extension direction and width direction by the first hole 57A and second hole 57B, the center axis (corresponding one of S1 to S3) of each of the switches 42A to 42C becomes substantially coaxial with the movement axis (corresponding one of M1 to M3) of the corresponding pusher (corresponding one of 22A to 22C). By the position of the board unit 35 being set as described above, each of the switches 42A to 42C is disposed at such a position that it properly transitions to the closed position by movement of the corresponding pusher (corresponding one of 22A to 22C) from the neutral position. Specifically, by setting the position of the board unit 25 relative to the unit exterior portion. 16 and base 17 by the first hole 57A and second hole 57B, each of the switches 42A to 42C can easily be disposed at such a position that it properly transitions to the closed position by movement of the corresponding pusher (corresponding one of 22A to 22C) from the neutral position.

Additionally, by simply abutting the planar cover portion outer surface 56B of the cover portion 41 upon the installation surface 58 of the base 17, the position of the board unit 25 is set in the thickness direction relative to the unit exterior portion 16 and base 17. Therefore, the position setting of the board unit 25 relative to the unit exterior portion 16 and base 17 in the thickness direction can also be easily executed.

When a treatment is performed by using the energy treatment instrument 2, the sheath 11 and blade 12 are inserted into the body. Then, the treatment portion 13 of the blade 12 is put in contact with the treated target. In this state, in any one of the pushers 22A to 22C, the button portion (one of 31A to 31C) is pushed, and an energy operation is input. Thereby, the switch (corresponding one of 42A to 42C), which corresponds to the pushed button portion (one of 31A to 31C), enters the closed state, and the input of the energy operation is detected by the energy source unit 8. By the input of the energy operation in any one of the button portions 31A to 31C being detected, high-frequency electric power is supplied from the energy source unit 8 to the treatment portion 13, and the treatment portion 13 treats the treated target by using the supplied high-frequency electric power. In the meantime, when an energy operation was input by the button portion 31E, high-frequency electric power is supplied to the treatment portion 13, and ultrasonic vibration is transmitted to the treatment portion 13.

In the pusher (corresponding one of 22A to 22C) in which the button portion (corresponding one of 31A to 31C) was pushed, the external force application portion (corresponding one of 32A to 32C) moves from the neutral state, and the external force acting on the cover portion 41 varies. Thereby, the elastic deformation portion (corresponding one of 52A to 52C), which corresponds to the pusher (corresponding one of 22A to 22C) that has moved from the neutral state, elastically deforms from the neutral shape. Then, a pushing force acts on the corresponding switch (corresponding one of 42A to 42C) from the elastic deformation portion (corresponding one of 52A to 52C) which has elastically deformed from the neutral shape. The switch (corresponding one of 42A to 42C), on which the pushing force acts from the corresponding elastic deformation portion (corresponding one of 52A to 52C), enters the closed state, by the movable contact portion (corresponding one of 46A to 46C) coming in contact with the fixed contact portion (corresponding one of 45A to 45C). In the present embodiment, since the cover portion 41 is provided, the external force application portion (corresponding one of 32A to 32C) of the pusher (corresponding one of 22A to 22C) does not come in direct contact with each of the switches 42A to 42C. However, since the cover portion 41 is provided with the elastic deformation portions 52A to 52C, each of the elastic deformation portions 52A to 52C elastically deforms from the neutral shape by the pusher (corresponding one of 22A to 22C) moving from the neutral state. Further, by each of the elastic deformation portions 52A to 52C elastically deforming, the pushing force can properly be exerted on the corresponding switch (corresponding one of 42A to 42C), and the switch (corresponding one of 42A to 42C) can properly be set in the closed state.

Each of the abutment surface portions 51A to 51C of the cover portion 41 is recessed toward the base 17 side, even in the neutral state of the pusher (corresponding one of 22A to 22C). Thus, without increasing the amount of operational force for pushing the button portion (corresponding one of 31A to 31C) in each of the pushers 22A to 22C, the corresponding elastic deformation portion (corresponding one of 52A to 52C) can properly be elastically deformed from the neutral shape, and the corresponding switch (corresponding one of 42A to 42C) can properly be set in the closed state. Besides, in each of the abutment surface portions 51A to 51C of the cover portion 41, by adjusting the recess dimension (corresponding one of L1 to L3) in the neutral state of the corresponding pusher (corresponding one of 22A to 22C), it is possible to adjust the stroke of the pusher (corresponding one of 22A to 22C) from the neutral state to the closed state of the switch (corresponding one of 42A to 42C).

If the treatment using the energy treatment instrument 2 is finished, the sheath 11 and blade 12 are detached from the held unit 3, and the held unit 3 is subjected to a thermal sterilization process by autoclave sterilization or the like. In the thermal sterilization process, there is a case in which a pressure acts on the held unit 3, and liquid enters the space in which the board unit 25 is disposed in the inside of the held unit 3 (held casing 5).

In the present embodiment, however, liquid-tightness is kept between the cover portion 41 and the non-exposed portion 37 of the switch board 35, and liquid is prevented from flowing from the outside of the board unit 25 into the non-exposed portion 37 of the switch board 35. Thus, even when liquid flows in the inside of the held unit 3, the flow of the liquid into the non-exposed portion 37 is effectively prevented, and the contact of the liquid with the switches 42A to 42C, which are disposed on the non-exposed portion 37, can be prevented. Since the contact of the liquid with the switches 42A to 42C is prevented, it is possible to properly prevent a defect in actuation of the switches 42A to 42C.

As described above, in the present embodiment, the contact with the switches 42A to 42C of the liquid, which has flowed into the space where the board unit 25 is disposed, can effectively be prevented, and the disposition of the board unit 25 and the assembly of the operation input unit 15 can easily be performed.

(Modifications)

Figure 8:
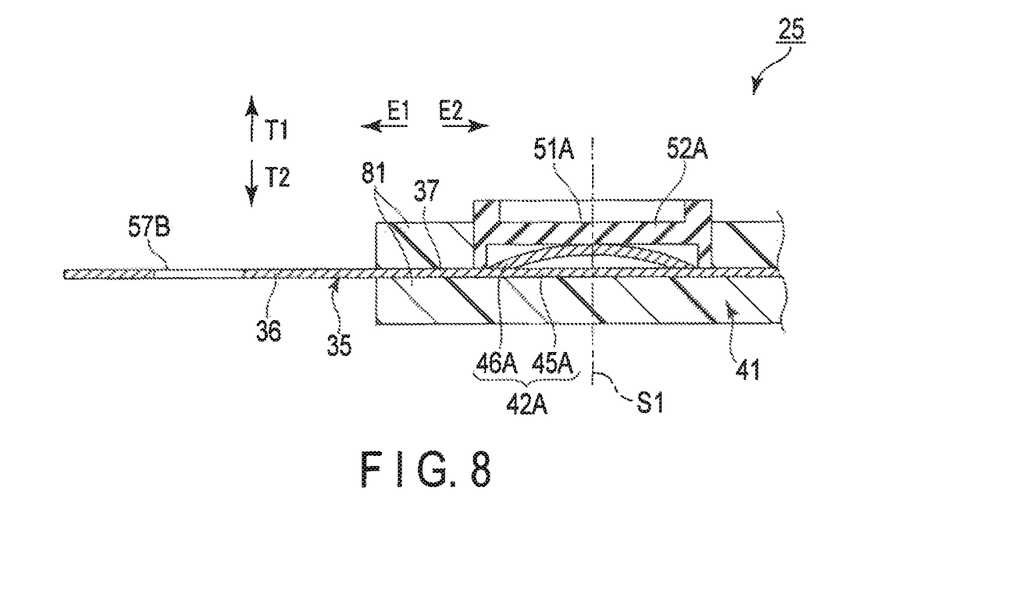
FIG. 8 is a cross-sectional view which schematically illustrates a board unit according to a first modification, by a cross section perpendicular to the width direction.

In the meantime, in the first embodiment, although the entirety of the cover portion 41 is formed of an elastic material, the restriction to this is unnecessary. For example, as illustrated in FIG. 8 as a first modification, only the elastic deformation portions 52A to 52C may be formed of an elastic material. In the present modification, that part of the cover portion 41, which is other than the elastic deformation portions 52A to 52C, is a rigid cover portion 81 which is formed of, for example, a hard resin. Incidentally, in FIG. 8, only the vicinity of the switch 42A is illustrated, and the depiction of the vicinity of the switch 42B and the vicinity of the switch 42C is omitted. In this modification, too, each of the elastic deformation portions 52A to 52C is formed in the abutment surface portion (corresponding one of 51A to 51C), on which the corresponding pusher (corresponding one of 51A to 51C) abuts, and in the vicinity of the abutment surface portion (corresponding one of 51A to 51C). In addition, each of the elastic deformation portions 52A to 52C is formed in an abutment portion which abuts on the movable contact portion (corresponding one of 46A to 46C) of the corresponding switch (corresponding one of 42A to 42C), and in the vicinity of the abutment portion. Thus, in the present modification, like the first embodiment, by the pusher (corresponding one of 22A to 22C) moving from the neutral state, each of the elastic deformation portions 52A to 52C elastically deforms from the neutral shape, and a pushing force acts on the switch (corresponding one of 42A to 42C). Thereby, also in this modification, by each of the elastic deformation portions 52A to 52C elastically deforming from the neutral shape, the movable contact portion (corresponding one of 46A to 46C) comes in contact with the fixed contact portion (corresponding one of 45A to 45C) in the corresponding switch (corresponding one of 42A to 42C), and the switch (corresponding one of 42A to 42C) enters the closed state.

In the present modification, the cover portion 41 is formed by double injection molding, which employs two kinds of movable dies (a first movable die and a second movable die) which have movable side cavities with mutually different shapes. For example, the rigid cover portion 81 is formed by injecting a hard resin in an injection cavity (a first injection cavity) which is formed between the first movable die and the fixed die. In addition, after the rigid cover portion 81 is formed, silicone rubber is injected in an injection cavity (a second injection cavity) which is formed between the second movable die and the fixed die, thereby forming the elastic deformation portions 52A to 52C.

Figure 9:
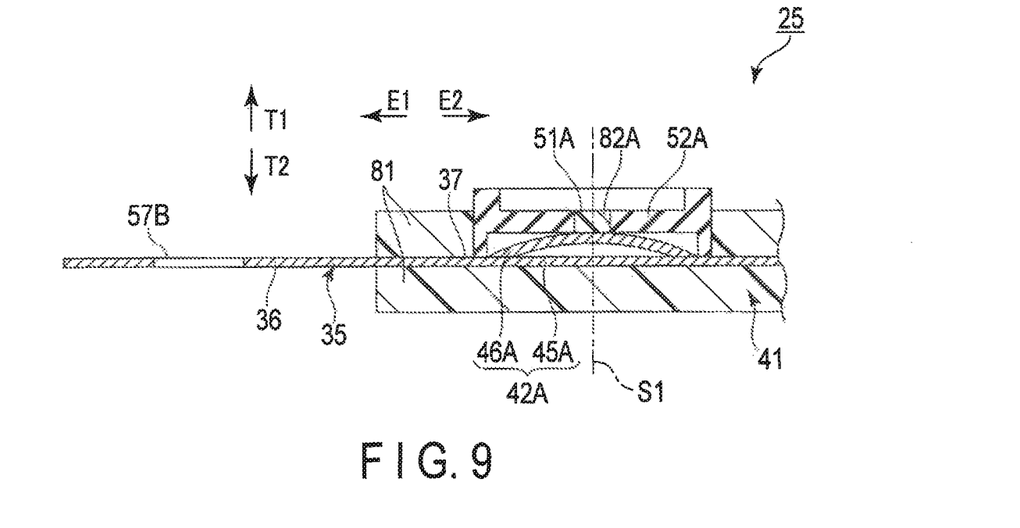
FIG. 9 is a cross-sectional view which schematically illustrates a board unit according to a second modification, by a cross section perpendicular to the width direction.

Additionally, in a second modification illustrated in FIG. 9, the cover portion 41 is provided with rigid abutment portions 82A to 82C which are formed of a hard resin material. Each of the rigid abutment portions 82A to 82C abuts on the movable contact portion (corresponding one of 46A to 46C) of the corresponding switch (corresponding one of 42A to 42C). In addition, the abutment surface portion (corresponding one of 51A to 51C), on which the external force application portion (corresponding one of 32A to 32C) of the pusher (corresponding one of 22A to 22C) abuts, is formed on each of the rigid abutment portions 82A to 82C. Incidentally, in FIG. 9, only the vicinity of the switch 42A is illustrated, and the depiction of the vicinity of the switch 42B and the vicinity of the switch 42C is omitted.

In the present modification, each of the elastic deformation portions 52A to 52C is formed in a cylindrical shape having the center agreeing with the center axis (corresponding one of S1 to S3) of the corresponding switch (corresponding one of 42A to 42C), and is formed in such a state as to surround the rigid abutment portion (corresponding one of 82A to 82C). In addition, that part of the cover portion 41, which is other than the elastic deformation portions 52A to 52C and rigid abutment portions 82A to 82C, is a rigid cover portion 81 which is formed of, for example, a hard resin. In the present modification, each of the elastic deformation portions 52A to 52C does not abut on the movable contact portion (corresponding one of 46A to 46C) of the corresponding switch (corresponding one of 42A to 42C), nor does the external force application portion (corresponding one of 32A to 32C) of the corresponding pusher (corresponding one of 22A to 22C) abut on each of the elastic deformation portions 52A to 52C. However, each of the elastic deformation portions 52A to 52C is formed near the abutment surface portion (corresponding one of 51A to 51C) on which the corresponding pusher (corresponding one of 22A to 22C) abuts, and is formed near the rigid abutment portion (corresponding one of 82A to 82C) which abuts on the movable contact portion (corresponding one of 46A to 46C) of the corresponding switch (corresponding one of 42A to 42C). Thus, in this modification, too, each of the elastic deformation portions 52A to 52C elastically deforms from the neutral shape by the pusher (corresponding one of 22A to 22C) moving from the neutral state. By each of the elastic deformation portions 52A to 52C elastically deforming, a pushing force acts on the corresponding switch (corresponding one of 42A to 42C) from the rigid abutment portion (corresponding one of 82A to 82C). Accordingly, also in this modification, by each of the elastic deformation portions 52A to 52C elastically deforming from the neutral shape, the movable contact portion (corresponding one of 46A to 46C) comes in contact with the fixed contact portion (corresponding one of 45A to 45C) in the corresponding switch (corresponding one of 42A to 42C), and the switch (corresponding one of 42A to 42C) enters the closed state.

In the present modification, too, the cover portion 41 is formed by double injection molding, which employs two kinds of movable dies (a first movable die and a second movable die) which have movable side cavities with mutually different shapes. For example, the rigid cover portion 81 and rigid abutment portions 82A to 82C are formed by injecting a hard resin in an injection cavity (a first injection cavity) which is formed between the first movable die and the fixed die. In addition, after the rigid cover portion 81 and rigid abutment portions 82A to 82C are formed, silicone rubber is injected in an injection cavity (a second injection cavity) which is formed between the second movable die and the fixed die, thereby forming the elastic deformation portions 52A to 52C.

In the first embodiment, first modification and second modification, the cover portion 41 of the board unit 25 is provided with the elastic deformation portions (52A to 52C). In addition, by each of the elastic deformation portions (52A to 52C) elastically deforming in accordance with the variation of the external force from the outside, the pushing force acts on the corresponding switch (corresponding one of 42A to 42C).

Additionally, in the present embodiment, the first hole 57A and second hole 57B are provided in the board unit 25, but the restriction to this is unnecessary. For example, in a third modification illustrated in FIG. 10, only the hole (first hole) 57A is provided on the proximal side (one side of the extension direction) with respect to the cover portion 41, and no hole is provided on the distal side with respect to the cover portion 41. In the present modification, the position of the board unit 25 is set relative to the base 17 and unit exterior portion 16 in the extension direction, at such a position that the hole 57A of the switch board 35 is opposed to the recess portion 61A of the unit exterior portion 16 and the recess portion 62A of the base 17. Specifically, the hole 57A functions as a first position setting portion which sets the position of the board unit 25 relative to the base 17 in the extension direction. In addition, by engaging the fixing pin 63A, which is inserted through the hole 57A, with the recess portion 61A of the unit exterior portion 16 and the recess portion 62A of the base 17, the board unit 25 is attached to the unit exterior portion 16 and base 17.

Figure 10:
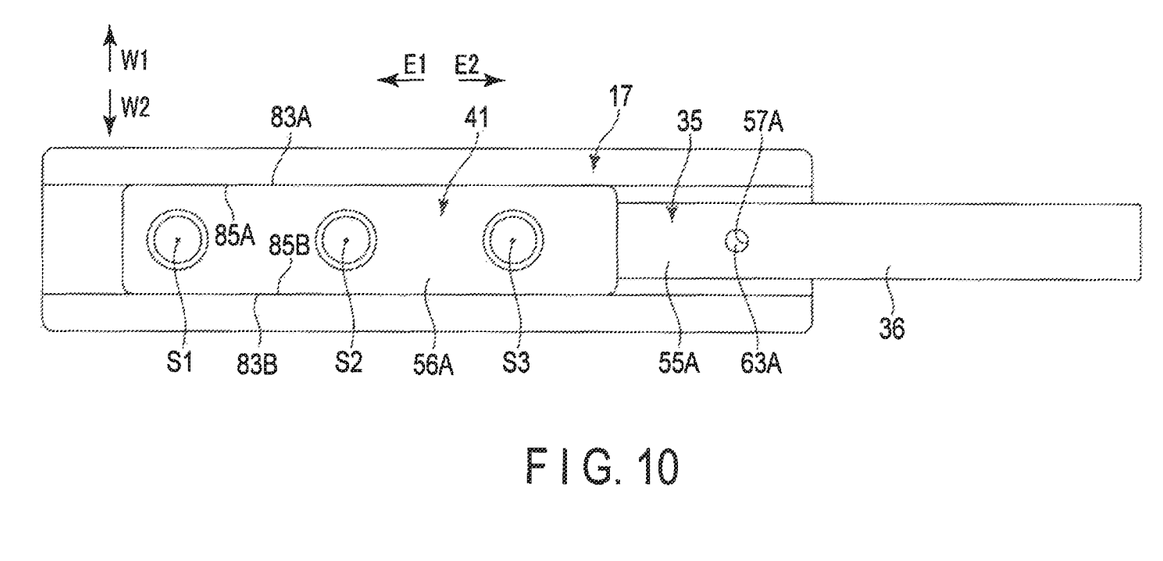
FIG. 10 is a schematic view illustrating a board unit and a base according to a third modification, as viewed from one side of a thickness direction of the board unit.

Besides, the cover portion 41 is provided with a cover portion end face 83A which is an end face on one side in the width direction, and a cover portion end face 83B which is an end face on the other side in the width direction. The base 17 is provided with a receiving surface 85A on which the cover portion end face 83A abuts, and a receiving surface 85B on which the cover portion end face 83B abuts. By the cover portion end face 83A abutting on the receiving surface 85A, and by the cover portion end face 83B abutting on the receiving surface 85B, the position of the board unit 25 is set in the width direction relative to the unit exterior portion 16 and base 17. Specifically, the cover portion end face 83A and cover portion end face 83B function as a second position setting portion which sets the position of the board unit 25 relative to the base 17 in the width direction. Furthermore, in this modification, too, the cover portion outer surface (second cover portion outer surface) 56B of the cover portion 41 functions as a third position setting portion which sets the position of the board unit 25 relative to the base 17 in the thickness direction.

Here, in a certain example, when the switch board 35 is fixed to the fixed die 71 in the manufacture, the hole (second hole) 57B, in addition to the hole (first hole) 57A, is provided in the switch board 35, like the first embodiment. By using the holes 57A and 57B, the position of the switch board 35 is set relative to the fixed die 71 in the extension direction and width direction. In addition, after the cover portion 41 is formed by injection molding, that part of the switch board 35 (the part where the hole 57B is located), which is located on the distal side with respect to the cover portion 41, is cut off.

Additionally, in another example, even when the switch board 35 is fixed to the fixed die 71 in the manufacture, only one hole (first hole) 57A is provided in the switch board 35. In addition, by using the hole 57A, the position of the switch board 35 is set relative to the fixed die 71 in the extension direction. In this case, the fixed die 71 is provided with two receiving portions (not shown), and the corresponding one of both end edges (not shown) in the width direction of the switch board 35 abuts on each of the receiving portions. By each of both end edges in the width direction of the switch board. 35 abutting on the corresponding receiving portion of the fixed die 71, the position of the switch board 35 is set relative to the fixed die 71 in the width direction.

In the first embodiment and the third modification, the board unit (25) is provided with the first position setting portion (57A; 57B) which sets the position in the extension direction (E1, E2) of the board unit (25) relative to the base (17), and the second position setting portion (57A, 57B; 83A, 83B) which sets the position in the width direction (W1, W2) of the board unit (25) relative to the base (17). In addition, the board unit (25) is provided with the third position setting portion (56B) which sets the position in the thickness direction (T1, T2) of the board unit (25) relative to the base (17).

Additionally, the above-described embodiments, etc., the non-exposed portion 37 of the switch board 35 is provided with the three switches 42A to 42C. However, it should suffice if the non-exposed portion 37 of the switch board 35 is provided with at least one switch (42A to 42C). Besides, it should suffice if the pusher (22A to 22C) is provided in association with each switch (42A to 42C).

Additionally, in the above-described embodiments, the board unit 25 is provided in the inside of the held unit 3 of the energy treatment instrument 2, and the operation input unit 15 including the board unit 25 is provided in the held unit 3. However, the restriction to this is unnecessary. For example, in a certain modification, an imaging device, such as an underwater camera for use in water, may be provided with the above-described board unit 25 and operation input unit 15. In this case, the board unit 25 is disposed in the inside of the exterior casing of the imaging device. In this modification, too, in the board unit 25, the flow of liquid into the non-exposed portion 37 of the switch board 35 is prevented by the cover portion 41. Thus, even when liquid flowed in the inside of the exterior casing (the space in which the board unit 25 is disposed) by the pressure in water, the adhesion of liquid to the switch (42A to 42C) located on the non-exposed portion 37 can effectively be prevented.

In the above-described embodiments, etc., the switch board (35) of the board unit (25) includes the exposed portion (36) which is exposed to the outside of the board unit (25), the non-exposed portion (37) which is not exposed to the outside of the board unit (25), and the switch (42A to 42C) provided in the non-exposed portion (37). The non-exposed portion (37) of the switch board (35) is covered with the cover portion (41). The cover portion (41) is formed as one piece with the switch board (35) in the state in which liquid-tightness is kept between the cover portion (41) and the non-exposed portion (37), and liquid is prevented from flowing from the outside of the board unit (25) into the non-exposed portion (37).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A board unit comprising:
a switch board including an exposed portion which is exposed to an outside, a non-exposed portion which is not exposed to the outside, and a switch provided in the non-exposed portion; and
a cover portion covering the non-exposed portion of the switch board, the cover portion being formed as one piece with the switch board in a state in which liquid-tightness is kept between the cover portion and the non-exposed portion, thereby preventing liquid from flowing from the outside into the non-exposed portion;
a first position setting portion configured to set a position in an extension direction of the board unit relative to a base on which the board unit is disposed;
a second position setting portion configured to set a position in a width direction of the board unit relative to the base; and
a third position setting portion configured to set a position in a thickness direction of the board unit relative to the base.

2. The board unit of claim 1, wherein the cover portion includes an elastic deformation portion configured to elastically deform in accordance with a variation of an external force from the outside, thereby exerting a pushing force on the switch.

3. The board unit of claim 2, wherein the switch includes a fixed contact portion, and a movable contact portion configured to move into a state of contact with the fixed contact portion by the pushing force acting on the switch in accordance with the elastic deformation of the elastic deformation portion.

4. The board unit of claim 1, wherein a first hole is formed in the board unit, the first hole penetrating the board unit in the thickness direction and functioning as the first position setting portion.

5. The board unit of claim 4, wherein a second hole is formed in the board unit, the second hole penetrating the board unit in the thickness direction at a position spaced apart from the first hole in the extension direction, and cooperating with the first hole to function as the second position setting portion.

6. The board unit of claim 1, wherein the switch board includes an electrical path portion which is electrically connected to the switch, and through which an electric current that is supplied to the switch flows.

7. An operation input unit comprising:
the board unit of claim 1;
a button portion configured to be pushed in an operation input; and
an external force application portion configured to move along a movement axis by the button portion being pushed, and configured to vary an external force acting on the cover portion of the board unit in accordance with the movement.

8. The operation input unit of claim 7, wherein the cover portion includes an abutment surface portion which is provided on an outer surface of the cover portion, and on which the external force application portion abuts in a neutral state in which the button portion is not pushed, and
the external force application portion is configured to recess the abutment surface portion in the neutral state by the external force on the cover portion.

9. An energy treatment instrument comprising:
the operation input unit of claim 7; and
a treatment portion configured to be supplied with energy for use in a treatment based on the operation input in the button portion, and configured to perform the treatment by using the supplied energy.

* * * * *